(12) United States Patent
Wilkowske et al.

(10) Patent No.: US 8,273,285 B2
(45) Date of Patent: Sep. 25, 2012

(54) STEERABLE CATHETER AND METHODS OF MAKING THE SAME

(75) Inventors: Eric John Wilkowske, North Oaks, MN (US); Allan Manuel Fuentes, Mound, MN (US); Xiaoping Guo, Eden Prairie, MN (US); Xuan Yen Khieu, Maple Grove, MN (US); Linda Kay Nemec, Andover, MN (US); Richard E. Stehr, Stillwater, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 985 days.

(21) Appl. No.: 11/033,098

(22) Filed: Jan. 10, 2005

(65) Prior Publication Data

US 2006/0151923 A1 Jul. 13, 2006

(51) Int. Cl.
B29C 43/00 (2006.01)

(52) U.S. Cl. ........................................................ 264/500

(58) Field of Classification Search ................. 623/1.32, 623/1; 606/198, 192; 604/96, 97, 98; 600/139, 600/140
See application file for complete search history.

(56) References Cited

U.S. PATENT DOCUMENTS

| | | | |
|---|---|---|---|
| 4,934,049 A | 6/1990 | Kiekhafer et al. | 29/883 |
| 4,960,134 A | 10/1990 | Webster, Jr. | 128/786 |
| 5,047,026 A | 9/1991 | Rydell | 606/48 |
| 5,125,895 A | 6/1992 | Buchbinder et al. | 604/95 |
| 5,125,896 A | 6/1992 | Hojeibane | 604/95 |
| 5,269,757 A | 12/1993 | Fagan et al. | 604/95 |
| 5,277,199 A | 1/1994 | DuBois et al. | 128/772 |
| 5,318,525 A | 6/1994 | West et al. | 604/95 |
| 5,327,889 A | 7/1994 | Imran | 128/642 |
| 5,327,906 A | 7/1994 | Fideler et al. | |
| 5,342,301 A * | 8/1994 | Saab | 604/103.13 |
| 5,354,297 A | 10/1994 | Avitall | 606/45 |
| 5,364,351 A | 11/1994 | Heinzelman et al. | |
| 5,383,923 A | 1/1995 | Webster, Jr. | 607/125 |

(Continued)

FOREIGN PATENT DOCUMENTS

EP  1 205 208  5/2002

(Continued)

*Primary Examiner* — Brian Szmal
*Assistant Examiner* — Fangemonique Smith
(74) *Attorney, Agent, or Firm* — Wiley Rein LLP

(57) ABSTRACT

The present invention is a method of manufacturing a flexible tubular body for catheter, sheath or similar medical device. The method comprises pre-extruding an inner layer of the body from a thermoplastic polymer and then pulling the inner layer over a mandrel and tightening the layer down. If wire lumens were not integrally formed in the inner layer when pre-extruded, then two polymer spaghetti tubes, each with wire lumens, are laid 180 degrees apart axially along the outer surface of the inner layer. Deflection wires are then fed into the wire lumens. A cylindrical wire braid is woven or pulled over the inner layer (and the spaghetti tubes, as the case may be) and tightened down. The aforementioned components are then encased in an outer polymer layer. A heat-shrinkable tube is then placed over the outer layer. A pressurized fluid is injected into each wire lumen to maintain the internal diameter of each wire lumen at a diameter that is greater than the diameter of the deflection wire received in each wire lumen. Heat is then applied to the body and heat-shrinkable tube to cause the layers to laminate together. Once the newly laminated body has sufficiently cooled, the heat-shrinkable tube is removed from the body.

32 Claims, 3 Drawing Sheets

U.S. PATENT DOCUMENTS

| | | | | |
|---|---|---|---|---|
| 5,389,073 | A | 2/1995 | Imran | 604/95 |
| 5,391,147 | A | 2/1995 | Imran et al. | 604/95 |
| 5,395,328 | A | 3/1995 | Ockuly et al. | 604/95 |
| 5,395,329 | A | 3/1995 | Fleischhacker et al. | |
| 5,397,304 | A | 3/1995 | Truckai | 604/95 |
| 5,423,772 | A | 6/1995 | Lurie et al. | 604/282 |
| 5,427,119 | A | 6/1995 | Swartz et al. | 128/772 |
| 5,431,168 | A | 7/1995 | Webster, Jr. | 128/658 |
| 5,445,148 | A | 8/1995 | Jaraczewski et al. | 128/642 |
| 5,478,330 | A | 12/1995 | Imran et al. | 604/282 |
| 5,487,385 | A | 1/1996 | Avitall | 128/642 |
| 5,487,757 | A | 1/1996 | Truckai et al. | 607/122 |
| 5,497,774 | A | 3/1996 | Swartz et al. | 128/658 |
| 5,533,967 | A | 7/1996 | Imran | 604/95 |
| 5,545,200 | A | 8/1996 | West et al. | 607/122 |
| 5,549,581 | A | 8/1996 | Lurie et al. | 604/282 |
| 5,564,440 | A | 10/1996 | Swartz et al. | 128/898 |
| 5,575,766 | A | 11/1996 | Swartz et al. | 604/53 |
| 5,588,964 | A | 12/1996 | Imran et al. | 604/95 |
| 5,611,777 | A | 3/1997 | Bowden et al. | 604/95 |
| 5,628,316 | A | 5/1997 | Swartz et al. | 128/657 |
| 5,640,955 | A | 6/1997 | Ockuly et al. | 128/642 |
| 5,643,231 | A | 7/1997 | Lurie et al. | 604/282 |
| 5,656,028 | A | 8/1997 | Swartz et al. | 604/53 |
| 5,656,029 | A | 8/1997 | Imran et al. | 604/95 |
| 5,656,030 | A | 8/1997 | Hunjan et al. | 604/95 |
| 5,662,608 | A * | 9/1997 | Imran et al. | 604/103.07 |
| 5,690,611 | A | 11/1997 | Swartz et al. | 604/53 |
| 5,715,818 | A | 2/1998 | Swartz et al. | 128/642 |
| 5,722,963 | A | 3/1998 | Lurie et al. | 604/282 |
| 5,725,512 | A | 3/1998 | Swartz et al. | 604/280 |
| 5,779,669 | A | 7/1998 | Haissaguerre et al. | 604/95 |
| 5,800,413 | A | 9/1998 | Swartz et al. | 604/280 |
| 5,810,730 | A | 9/1998 | Swartz et al. | 600/434 |
| 5,814,027 | A | 9/1998 | Hassett et al. | 604/286 |
| 5,814,028 | A | 9/1998 | Swartz et al. | 604/280 |
| 5,814,029 | A | 9/1998 | Hassett | 604/281 |
| 5,827,278 | A | 10/1998 | Webster | 606/41 |
| 5,833,673 | A | 11/1998 | Ockuly et al. | 604/281 |
| 5,836,947 | A | 11/1998 | Fleischman et al. | 606/47 |
| 5,840,027 | A | 11/1998 | Swartz et al. | 600/433 |
| 5,842,984 | A | 12/1998 | Avitall | 600/374 |
| 5,843,031 | A | 12/1998 | Hermann et al. | 604/95 |
| 5,843,076 | A | 12/1998 | Webster, Jr. et al. | 606/41 |
| 5,846,223 | A | 12/1998 | Swartz et al. | 604/53 |
| 5,861,024 | A | 1/1999 | Rashidi et al. | |
| 5,868,733 | A | 2/1999 | Ockuly et al. | 606/10 |
| 5,879,296 | A | 3/1999 | Ockuly et al. | 600/374 |
| 5,885,278 | A | 3/1999 | Fleischman | 606/41 |
| 5,897,529 | A | 4/1999 | Ponzi | 604/95 |
| 5,902,289 | A | 5/1999 | Swartz et al. | 604/281 |
| 5,916,213 | A | 6/1999 | Haissaguerre et al. | 606/41 |
| 5,916,214 | A | 6/1999 | Cosio et al. | 606/41 |
| 5,921,924 | A | 7/1999 | Avitall | 600/374 |
| 5,921,957 | A * | 7/1999 | Killion et al. | 604/96.01 |
| 5,931,811 | A | 8/1999 | Haissaguerre et al. | 604/95 |
| 5,944,690 | A | 8/1999 | Falwell et al. | 604/95 |
| 5,947,938 | A | 9/1999 | Swartz et al. | 604/280 |
| 5,993,462 | A | 11/1999 | Pomeranz et al. | 606/129 |
| 6,001,085 | A | 12/1999 | Lurie et al. | 604/282 |
| 6,002,955 | A | 12/1999 | Willems et al. | 600/374 |
| 6,022,341 | A | 2/2000 | Lentz | 604/523 |
| 6,024,722 | A | 2/2000 | Rau et al. | |
| 6,030,371 | A * | 2/2000 | Pursley | 604/527 |
| 6,033,403 | A | 3/2000 | Tu et al. | 606/41 |
| 6,048,329 | A | 4/2000 | Thompson et al. | 604/95 |
| 6,068,629 | A | 5/2000 | Haissaguerre et al. | 606/41 |
| 6,071,274 | A | 6/2000 | Thompson et al. | 604/528 |
| 6,090,084 | A | 7/2000 | Hassett et al. | 604/281 |
| 6,090,104 | A | 7/2000 | Webster, Jr. | 606/41 |
| 6,138,043 | A | 10/2000 | Avitall | 600/377 |
| 6,156,018 | A | 12/2000 | Hassett | 604/281 |
| 6,156,034 | A | 12/2000 | Cosio et al. | 606/41 |
| 6,200,315 | B1 | 3/2001 | Gaiser et al. | 606/41 |
| 6,203,525 | B1 | 3/2001 | Whayne et al. | 604/95.01 |
| 6,203,531 | B1 | 3/2001 | Ockuly et al. | 604/264 |
| 6,219,582 | B1 | 4/2001 | Hofstad et al. | 607/122 |
| 6,241,754 | B1 | 6/2001 | Swanson et al. | 607/99 |
| 6,308,091 | B1 | 10/2001 | Avitall | 600/374 |
| 6,371,955 | B1 | 4/2002 | Fuimaono et al. | 606/41 |
| 6,447,507 | B1 | 9/2002 | Bednarek et al. | 606/41 |
| 6,466,811 | B1 | 10/2002 | Hassett | 600/374 |
| 6,526,302 | B2 | 2/2003 | Hassett | 600/374 |
| 6,540,755 | B2 | 4/2003 | Ockuly et al. | 606/108 |
| 6,582,536 | B2 | 6/2003 | Shimada | |
| 6,623,424 | B2 * | 9/2003 | Hayakawa et al. | 600/139 |
| 6,709,455 | B1 * | 3/2004 | Chouinard | 623/1.32 |
| 6,913,617 | B1 * | 7/2005 | Reiss | 623/1.15 |
| 6,951,554 | B2 * | 10/2005 | Johansen et al. | 604/509 |

FOREIGN PATENT DOCUMENTS

| | | |
|---|---|---|
| GB | 1 170 018 | 11/1969 |

* cited by examiner

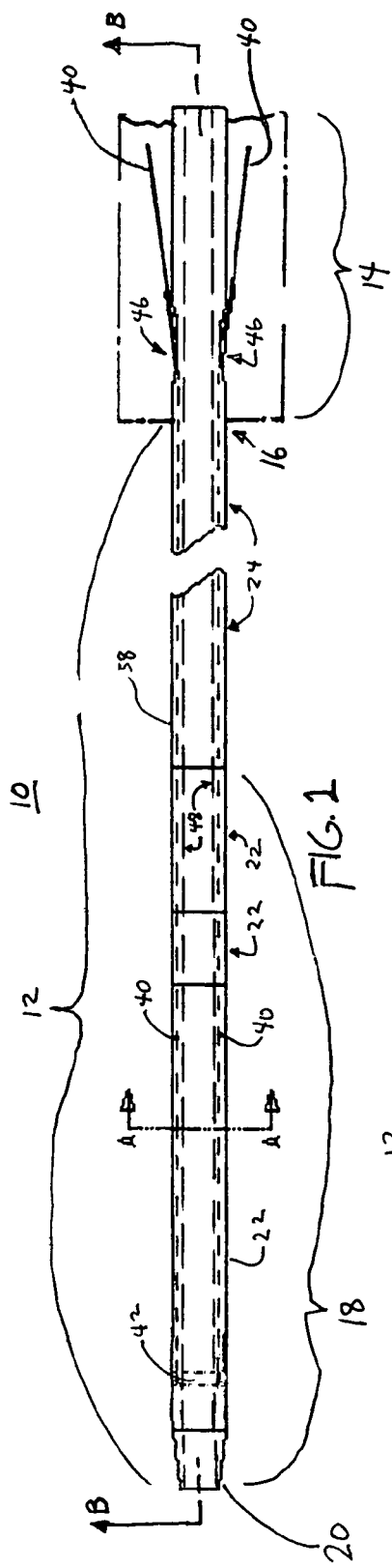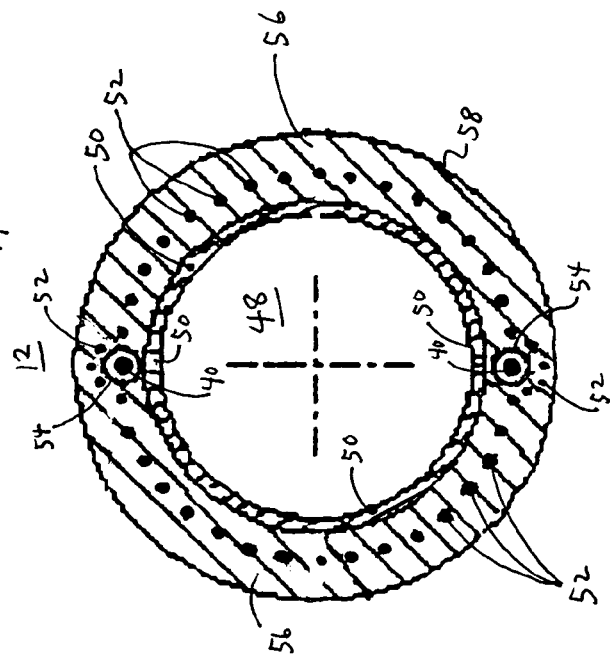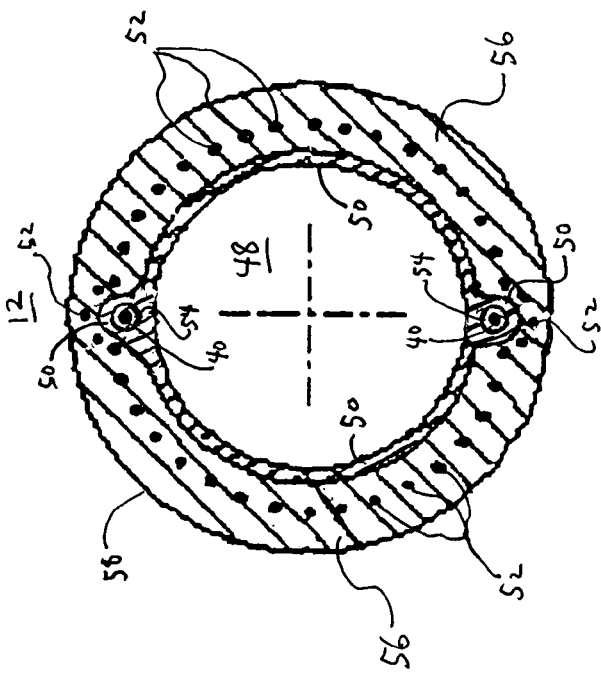
FIG. 1
FIG. 2
FIG. 3

STEERABLE CATHETER AND METHODS OF MAKING THE SAME

FIELD OF THE INVENTION

The present invention relates to catheters and sheaths and methods of making and using catheters and sheaths. More particularly, the present invention relates to the flexible tubular bodies of steerable catheters or sheaths and methods of making and using such bodies.

BACKGROUND OF THE INVENTION

A current method in the art used to manufacture flexible tubular bodies of steerable catheters or sheaths is to form the body on a mandrel using multiple layers: an inner liner intended to define the central lumen of the body; a layer of wire braid for reinforcing the body; and an outer thermoplastic jacket. The inner liner is pulled over the mandrel and tightened down. Deflection wires used to deflect the distal tip of the body are laid axially along the inner liner. The layer of wire braid is pulled or woven over the inner liner and deflection wires. After the wire braid is tightened down, the entire body is encased in a thermoplastic outer jacket. The outer jacket is then encased in heat-shrink material and heated. The heat causes the thermoplastic jacket layer to flow, which, when teamed with the pressure from the heat-shrink material, causes the thermoplastic outer jacket to impregnate the wire braid and embed the deflection wires. This consolidates the body into one integral unit.

Embedding the deflection wires in the flexible tubular body via the action of the thermoplastic polymer teamed with the heat-shrink material allows the deflection wires to create their own wire lumens. However, the deflection wires and the resulting wire lumens end up being approximately equal in diameter. This creates three related difficulties. First, significant deflection wire actuation friction is created between the walls of the wire lumens and the deflection wires as an operator attempts to deflect the body by moving the deflection wires. This actuation friction increases the difficulty in operating the deflection wires. Second, as the distal end of the body is deflected (bent) through the movement of the deflection wires, the wire braid embedded in the outer wall of the body is also flexed. As the wire braid flexes, the forces created can deform the central lumen. This can cause the wire braid to lock down on the deflection wires and the wire lumens. This greatly increases the deflection wire actuation friction and can prevent movement of the deflection wires as the wire lumens are deformed from a circular shape into an ovular shape. The third problem is that as the deflection wires are "locked down" in the bent body, the deflection wires and body loses the ability to spring back to the original shape as the force on the deflection wires from the operator at the proximal end is removed.

To overcome the aforementioned difficulties, U.S. Pat. No. 6,582,536 to Shimada, which issued Jun. 24, 2003, teaches creating flexible tubular bodies with lumens that are larger in diameter than the deflection wires to be received in the lumens. To achieve such an arrangement, a lumen defining wire is embedded in the outer thermoplastic jacket of the body to define a lumen. The lumen defining wire has a diameter that exceeds the diameter of the deflection wire to be received in the lumen. Once the oversized lumen is formed, the lumen defining wire is removed and the deflection wire is inserted into the oversized lumen.

The method taught in the Shimada patent helps reduce the deflection wire actuation friction and locking problems associated with deflection wires and their lumens. However, it does so at the cost of increased manufacturing complication, waste and, as a result, expense.

There is a need in the art for a less expensive method of manufacturing a flexible tubular body with deflection wires that generate less deflection wire actuation friction and are less likely to lock when the body is being deflected. There is also a need in the art for a flexible tubular body manufactured according to said method.

BRIEF SUMMARY OF THE INVENTION

The present invention, in one embodiment, is a method of manufacturing a flexible tubular body of a catheter, sheath or similar medical device. The method comprises pre-extruding an inner layer of the body from a thermoplastic polymer and then pulling the inner layer over a mandrel and tightening the layer down. If wire lumens were not integrally formed in the inner layer when pre-extruded, then two polymer spaghetti tubes, each with wire lumens, are laid 180 degrees apart axially along the outer surface of the inner layer. Deflection wires are then fed into the wire lumens. A cylindrical wire braid is woven or pulled over the inner layer (and the spaghetti tubes, as the case may be) and tightened down. The aforementioned components are then encased in an outer polymer layer. A heat-shrinkable tube is then placed over the outer layer. A pressurized fluid is injected into each wire lumen to maintain the internal diameter of each wire lumen at a diameter that is greater than the diameter of the deflection wire received in each wire lumen. Heat is then applied to the body and heat-shrinkable tube to cause the layers to laminate together. Once the newly laminated body has sufficiently cooled, the heat-shrinkable tube is removed from the body.

The present invention, in one embodiment, is a method of manufacturing a flexible tubular body of a catheter, sheath or similar medical device. The method comprises forming a wire lumen and injecting a fluid into the wire lumen. In one embodiment, a deflection wire is located in the wire lumen when the fluid is being injected.

In one embodiment, the fluid flows in a first end of the wire lumen and out an opposite end of the wire lumen. In one embodiment, the fluid is injected in a first end of the wire lumen, but the opposite end of the wire lumen is plugged so the fluid does not flow through the wire lumen.

In one embodiment, the fluid is a liquid. In another embodiment, the fluid is a gas. In one embodiment, the fluid is a gas at approximately 85 psig.

The present invention, in one embodiment, is a flexible tubular body of a catheter, sheath or similar medical device. The body comprises a deflection wire residing within a wire lumen having an inner diameter that exceeds the outer diameter of the deflection wire. During the manufacturing of the body, the wire lumen is injected with a fluid to prevent a reduction in the inner diameter.

In one embodiment, the body also includes an inner layer, an outer layer and a wire braid. The inner layer defines a central lumen. The outer layer surrounds the inner layer. The wire braid surrounds the inner layer and is impregnated by the outer layer.

In one embodiment, the wire lumen resides within at least a portion of the inner layer. For example, in such an embodiment, the wire lumen was pre-extruded with the inner layer during the manufacturing of the body. In another embodiment, the wire lumen resides within at least a portion of the outer layer. Specifically, the wire lumen is part of a pre-extruded spaghetti tube that was laid axially along an outer surface of the inner layer during the manufacturing of the body.

In one embodiment, the body also includes a fluid residue within wire lumen. The residue helps to lubricate the displacement of the deflection wire through the wire lumen.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 1 is a side view of a steerable catheter or sheath employing the flexible tubular body of the present invention.

FIG. 2 is a lateral cross section of one embodiment of the flexible tubular body of the steerable catheter or sheath taken along section line AA in FIG. 1.

FIG. 3 is a lateral cross section of another embodiment of the flexible tubular body taken along section line AA in FIG. 1.

DETAILED DESCRIPTION

Figure 4:
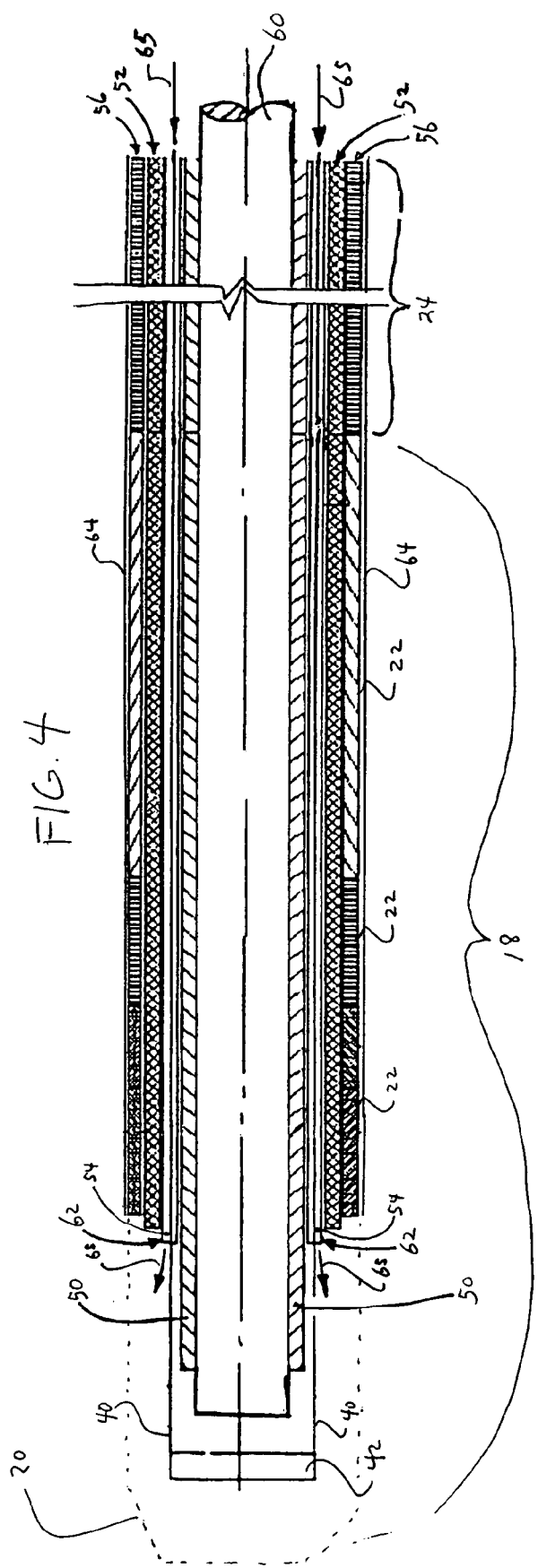
FIG. 4 is a longitudinal cross section of the body depicted in FIG. 2, as if taken along section line BB in FIG. 1, when being manufactured.

The present invention, in one embodiment, is a flexible tubular body for a steerable catheter, sheath or similar medical device that offers reduced deflection wire actuation friction and locking problems, but is less expensive and complicated to manufacture, as compared to prior art methods. During manufacturing of the flexible tubular body, oversized wire lumens are formed about deflection wires embedded in the wall of the body by injecting a pressurized fluid between the circumferential surfaces of the wire lumen and the deflection wire located therein.

For a discussion of a steerable catheter or sheath 10 employing the flexible tubular body 12 of the present invention, reference is now made to FIG. 1, which is a side view of the catheter or sheath 10. As shown in FIG. 1, the catheter or sheath 10 includes a generally tubular flexible body 12 and an actuation handle 14 coupled to a proximal end 16 of the body 12. A distal end 18 of the body 12 is adapted to deflect (i.e., bend) when actuated by the handle 14 and includes a soft tip 20 and a plurality of deflexing segments 22. The most proximal deflexing segment 22 is joined to a body segment 24 that extends to the proximal end 16.

As indicated by phantom lines in FIG. 1, a pair of deflection wires 40 extend through the body 12 from a pull ring 42 near the tip 20 until the wires 40 exit the body 12 via windows 46 in the actuator handle 14. The deflection wires 40 are coupled to an actuation mechanism in the handle 14 that causes the wires 40 to displace and, as a result, the distal end 18 to deflect.

As indicated by phantom lines in FIG. 1, in one embodiment, a central lumen 48 extends through the body 12 from the tip 20 to the handle 14. The central lumen 48 can be used to deliver medical fluids or equipment to a site within a patient.

As shown in FIG. 2, which is a lateral cross section of the flexible tubular body 12 taken along section line AA in FIG. 1, in one embodiment, the body 12 includes the central lumen 48, an inner layer 50, a cylindrical wire braid 52 employing wire with a flat or cylindrical cross-section, a pair of wire lumens 54 with deflection wires 40 received therein, an outer layer 56, and an outer circumferential surface 58. The outer layer 56 abuts against, and circumferentially encompasses, the inner layer 50, the wire braid 52 is embedded within the outer layer 56, and the wire lumens 54 are offset from each other about the central lumen 48 by approximately 180 degrees.

As illustrated in FIG. 2, in one embodiment, the wire lumens 54 exist within the outer layer 56. In another embodiment, as shown in FIG. 3, which is a cross section of the flexible tubular body 12 taken along section line AA in FIG. 1, the wire lumens 54 exist within the inner layer 50 such that, in one embodiment, the inner layer 50 is significantly thicker in the region of the wire lumens 54 to encompass the wire lumens 54 within the inner layer 50.

Regardless of the embodiment, as indicated in FIGS. 2 and 3, the inner diameter of the wire lumens 54 exceed the outer diameter of the deflection wires 40 received therein. The difference in diameters is sufficiently large that friction generated between the deflection wires 40 and the wire lumens 54 is minimized. Also, the likelihood that the deflection wires 40 will be locked up by the wire lumens 54 is minimized. However, the difference in diameters is still sufficiently small to allow the wire lumens 54 to adequately support the deflection wires 40 and prevent the wires 40 from buckling. In one embodiment, the difference between the inner diameter of a wire lumen 54 and the outer diameter of a deflection wire 40 therein is between approximately 0.002 inch and approximately 0.004 inch.

Figure 5:
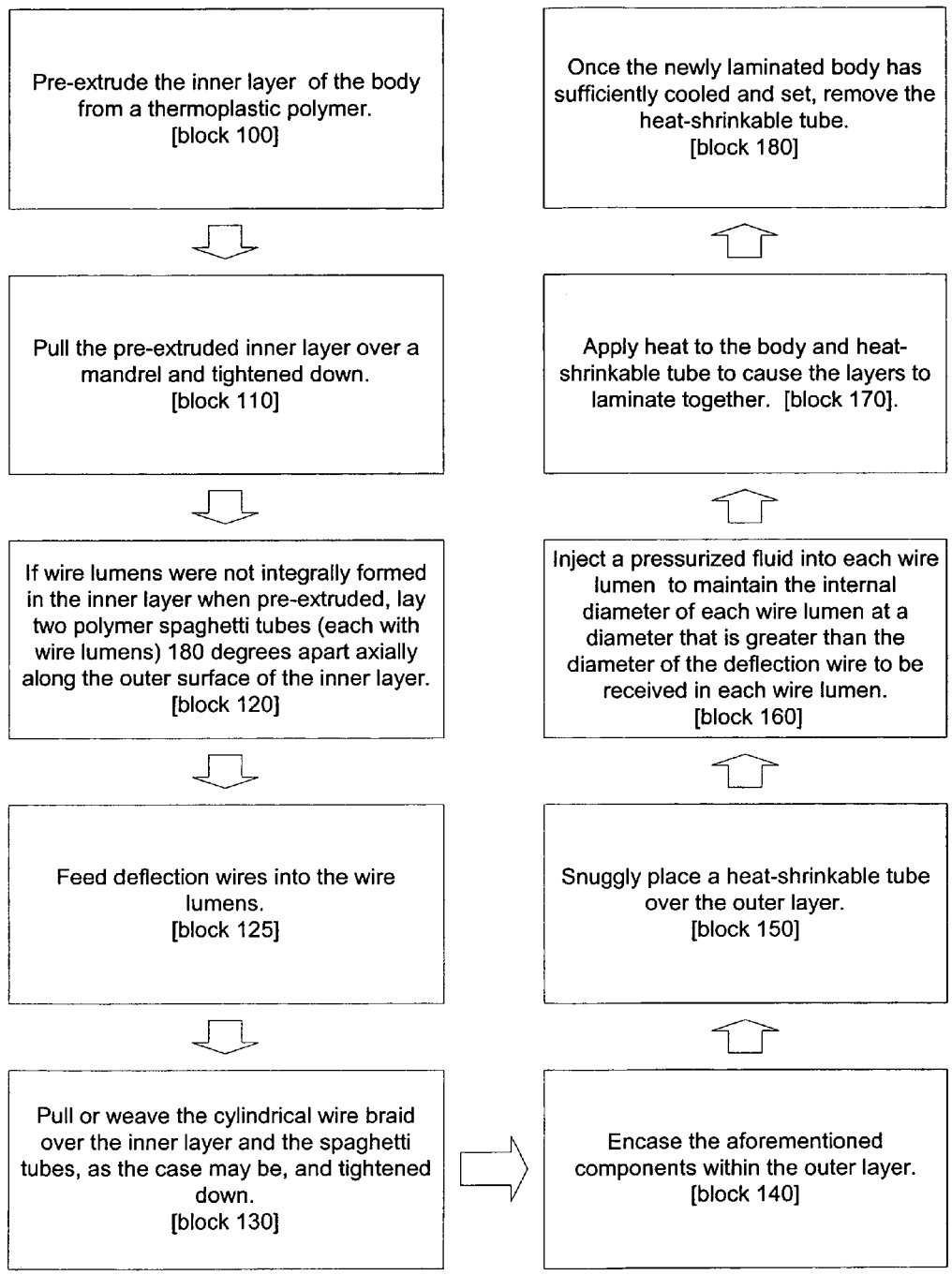
FIG. 5 is a flow chart outlining the method of manufacturing the body embodiments illustrated in FIGS. 2 and 3.

For a discussion regarding the manufacture of the above-discussed flexible tubular body 12, reference is now made to FIGS. 4 and 5. FIG. 4 is a longitudinal cross section of the body 12 depicted in FIG. 2 when being manufactured, as taken along section line BB in FIG. 1. FIG. 5 is a flow chart outlining the method of manufacturing the flexible tubular body embodiments illustrated in FIGS. 2 and 3.

As illustrated in FIGS. 4 and 5, in one embodiment, the inner layer 50 of the body 12 is pre-extruded from a thermoplastic polymer (e.g., polytetrafluoroethylene "PTFE", polyvinylidene fluoride "PVDF", polyetheretherketone "PEEK", etc.) [block 100]. The pre-extruded inner layer 50 is then pulled over a core rod or mandrel 60 and tightened down, as shown in FIG. 4 [block 110].

As illustrated in FIG. 4, in manufacturing the embodiment depicted in FIG. 2, two polymer spaghetti tubes 62 with wire lumens 54 for receiving the deflection wires 40 are laid 180 degrees apart axially along the outer surface of the inner layer 50 [block 120]. In one embodiment the spaghetti tubes 62 are pre-extruded from a polymer (e.g., polytetrafluoroethylene "PTFE", polyvinylidene fluoride "PVDF", polyetheretherketone "PEEK", etc.) In another embodiment the spaghetti tubes 62 are extruded as they are laid along the outer surface of the inner layer 50.

It should be noted, however, that the process of laying the spaghetti tubes 62 is not necessary when manufacturing the embodiment depicted in FIG. 3. This is because the wire lumens 54 of the embodiment depicted in FIG. 3 are extruded as an integral part of the inner layer 50 when the inner layer 50 is being extruded.

As shown in FIG. 4, in one embodiment, regardless of how the wire lumens 54 are formed, once the inner layer 50 exists on the mandrel 60, the deflection wires 40 are fed into the wire lumens 54 [block 125]. In another embodiment, the deflection wires 40 are fed into the wire lumens 54 later in the process, as discussed below.

As indicated in FIG. 4, the cylindrical wire braid 52 is pulled or woven over the inner layer 50 and, as the case may be, the spaghetti tubes 62. The wire braid 52 is then tightened down [block 130]. The entirety of the aforementioned components is then encased within the outer layer 56 [block 140]. For example, in one embodiment, the outer layer 56 is a pre-extruded layer that is pulled over the aforementioned components and tightened down. In another embodiment, the outer layer 56 is extruded over or sprayed onto the aforementioned components.

At the distal end 18 of the body 12, the outer layer 56 consists of the polymer material forming the deflexing segments 22 (e.g., polyether block amide "PEBA", polyvinylidene fluoride "PVDF", polyethylene terephthalate "PET", etc.). In one embodiment, the deflexing segments 22 are PEBA with durometer values that ranged between approximately 35 and approximately 55 on a type-D durometer. Along the body segment 24, the outer layer 56 consists of the polymer material forming the body segment 24 (e.g., polyether block amide "PEBA", polyvinylidene fluoride "PVDF", polyethylene terephthalate "PET", etc.). In one embodiment, the body segment 24 was PEBA with a durometer value of approximately 72 on a type-D durometer. Each polymer used for each deflexing segment 22 has a different deflexing compliance (i.e., durometer value) that is appropriate for the deflecting distal end 18 of a deflectable body 12 designed to deflect to specified curves.

As shown in FIG. 4, a heat-shrinkable tube 64 is snuggly placed over the outer layer 56 [block 150]. In one embodiment, the heat-shrinkable tube 64 is a polymeric material such as fluorinated ethylene-propylene copolymer "FEP", polytetrafluoroethylene "PTFE", or polyethylene terephthalate "PET". In one embodiment, the heat-shrinkable tube 64 has a shrink temperature ranging from approximately 190 degrees Celsius to approximately 220 degrees Celsius.

As indicated in FIG. 4, a pressurized fluid 65 (e.g., gases such as air, nitrogen, argon, carbon dioxide, etc. or liquids such as silicone gel fluid, silicone oil, etc.) is injected into each wire lumen 54 to maintain the internal diameter of each wire lumen 54 at a diameter that is greater than the diameter of the deflection wire 40 to be received in each wire lumen 54 [block 160]. In one embodiment, the pressurized fluid is injected into wire lumens 54 that are empty (i.e., the wire lumens 54 do not contain deflection wires 40 when being injected with the fluid). In another embodiment, as indicated in FIG. 4, the pressurized fluid is injected into wire lumens 54 that contains their respective deflection wires 40. In one embodiment, the fluid is maintained at a pressure of between approximately 50 psig and approximately 110 psig. In one embodiment, the fluid is air injected at approximately 85 psig.

In one embodiment, as indicated in FIG. 4, both ends of each wire lumen 54 are open such that the fluid 65 is injected in, for example, the proximal end of the wire lumen 54 and exits the distal end of the wire lumen 54. In other words, the fluid 65 flows through the wire lumen 54. In another embodiment, the distal end of the wire lumen 54 is sealed (e.g., by a UV adhesive) and the fluid 65 is injected in the proximal end such that the wire lumen 54 is pressurized, but the fluid 65 does not flow through the wire lumen 54.

Once the pressurized fluid is being injected into the wire lumens 54, heat is then applied to the body 12 [block 170]. The combination of the pressure from the heat-shrinkable tube 64 and the applied heat causes the aforementioned layers to laminate together, as illustrated in FIGS. 2 and 3. More specifically, the outer layer 56 melts and forcibly flows such that it impregnates the wire braid 52 and forms around and bounds with the inner layer 50 and, as the case may be, the spaghetti tubes 62. Because the wire lumens 54 are pressurized, their internal diameters are maintained and prevented from collapsing when the body 12 is subjected to the aforementioned pressure and heat.

In one embodiment, where the heat-shrinkable tube 64 is formed of FEP with a shrink temperature ranging from approximately 190 degrees Celsius to approximately 220 degrees Celsius, the body 12 and heat-shrinkable tube 64 are heated to within this temperature range. At this temperature range, the outer layer 56, which, in one embodiment, is formed of PEBA, melts and consolidates with the inner layer 50 and spaghetti tubes 62, which, in one embodiment, are formed of PTFE and chemically etched on their outer surfaces.

Once the newly laminated body 12 has sufficiently cooled and set, the heat-shrinkable tube 64 is removed from the body 12 [block 180]. If, as illustrated in FIG. 4, the wire lumens 54 were pressurized while containing their respective deflection wires 40, the body 12 is, generally speaking, ready to be formed into a catheter, sheath or similar medical device 10. The tip 20, shown in phantom lines in FIG. 4, and the handle 14 can then be added so the catheter or sheath 10 is formed as depicted in FIG. 1. If the wire lumens 54 were pressurized without containing their respective deflection wires 40, the deflection wires 40 must be inserted into the wire lumens 54 before the body 12 can be formed into a catheter or sheath 10.

In one embodiment, the polymeric material used for the inner layer 50 and, as the case may be, the spaghetti tubes 62, has a melting or softening point that is higher than those polymeric materials used for the outer layer 56 and the heat-shrinkable tube 64. In one embodiment, the polymeric materials used to form the inner and outer layers 50, 56 and, as the case may be, the spaghetti tubes 62, are chemically compatible such that they can be thermally bonded at the interfaces between the various polymeric materials.

In another embodiment, where the various polymeric materials are not necessarily chemically compatible such that they will thermally bond, the interfacing surfaces of the various materials will be subjected to physical or chemical surface modification to achieve reliable surface bonding. Physical surface modification includes plasma, corona, and laser surface treatments. Chemical surface modification refers to chemical etching methods.

Outright chemical compatibility between the various polymeric materials or surface modification to achieve reliable surface bonding is necessary to ensure that the body 12 is fully laminated during the lamination process into an integrated structure in the form of interfacial bonding by means of liquefying the outer layer 56. When heat is applied, the heat-shrinkable tube 64 starts to generate varying lamination pressure, which transfers inwards the thermal energy to liquefy the outer layer 56 during the lamination process.

To ensure that the outer layer 56 is completely liquefied during the lamination process, the shrink temperature of the heat-shrinkable tube 64 must be higher than the softening or melting temperature of the outer layer 56. The combination of the heat and pressure during lamination results in an integrated body 12 via polymer melt flow and interfacial bonding among all laminated components.

As indicated in FIG. 4, the mandrel 60 supports the central lumen 48 during the lamination process and prevents its collapse from the heat and pressure. As already discussed, the wire lumens 54 are pressurized via a fluid to prevent their collapse during the lamination process. The inflation fluid must be able to withstand the lamination temperature without thermally degrading, introducing contaminants into the polymeric material forming the wire lumens 54, or adversely impacting interfacial bonding. During lamination, the inflation pressure of the inflation fluid will act against the lamination pressure from the heat-shrinkable tube 64, keeping the wire lumens 54 open to their predefined dimensions.

Where the inflation fluid is lubricious (e.g., silicone gel fluid or oil), the fluid residue that remains in the wire lumen 54 helps to lubricate the displacement of the deflection wire 40. This decreases the friction generated between the deflection wire 40 and the wire lumen 54, thereby requiring less effort by a user to deflect the distal end 18 of the body 12. This also decreases the likelihood that the deflection wire 40 will lockup or bind within the wire lumen 54. To further decrease friction between the deflection wires 40 and the wire lumens 54, the deflection wires 40 can be coated with their own silicon or PTFE coatings.

Although the present invention has been described with reference to preferred embodiments, persons skilled in the art will recognize that changes may be made in form and detail without departing from the spirit and scope of the invention.

We claim:

1. A method of manufacturing a flexible tubular body for a catheter or sheath, the flexible tubular body comprising a melt-processable polymer, the method comprising:
    forming a wire lumen;
    placing a deflection wire in the wire lumen;
    injecting a fluid into the wire lumen; and
    melt-processing the flexible tubular body while the fluid and the deflection wire are in the wire lumen.

2. The method of claim 1, wherein the deflection wire is located in the wire lumen when the fluid is being injected.

3. The method of claim 1, wherein the fluid flows in a first end of the wire lumen and out an opposite end of the wire lumen.

4. The method of claim 1, wherein the fluid is injected in a first end of the wire lumen, but an opposite end of the wire lumen is plugged so the fluid does not flow through the wire lumen.

5. The method of claim 1, wherein the fluid is a gas.

6. The method claim 1, wherein the fluid is a liquid.

7. The method of claim 1, wherein the fluid is a gas injected at approximately 85 psig.

8. The method of claim 1, wherein the fluid is a liquid selected from the group consisting of silicone gel fluid and silicon oil.

9. The method of claim 1, wherein the fluid is a gas selected from the group consisting of air, nitrogen, argon, and carbon dioxide.

10. The method of claim 1, further comprising providing an inner layer.

11. The method of claim 10, further comprising defining a central lumen with the inner layer.

12. The method of claim 10, further comprising applying an outer layer about the inner layer.

13. The method of claim 12, wherein the inner layer is PTFE, the wire lumen is PTFE, and the outer layer is PEBA.

14. The method of claim 12, further comprising applying a wire braid about the inner layer.

15. The method of claim 14, wherein the wire braid is impregnated by the outer layer.

16. The method of claim 12, further comprising applying a layer of shrink-wrap about the outer layer.

17. The method of claim 16, wherein the shrink-wrap layer is FEP.

18. The method of claim 16, wherein the step of melt-processing the flexible tubular body while the fluid and the deflection wire are in the wire lumen comprises heating the shrink-wrap layer.

19. The method of claim 18, wherein the heating causes the inner and outer layers to bond.

20. The method of claim 18, wherein the shrink-wrap layer is heated to a temperature range of between approximately 190 degrees Celsius and 220 degrees Celsius to cause the shrink-wrap layer to shrink.

21. The method of claim 12, wherein the wire lumen exists within at least a portion of the inner layer.

22. The method of claim 21, wherein the wire lumen is co-extruded with the inner layer.

23. The method of claim 12, wherein the wire lumen exists within at least a portion of the outer layer.

24. The method of claim 23, wherein the wire lumen is pre-extruded as a spaghetti tube and laid along an outer surface of the inner layer prior to the application of the outer layer.

25. A catheter or sheath formed according to the method of claim 1.

26. The method of claim 1, wherein the deflection wire is placed in the wire lumen after the step of injecting a fluid into the wire lumen.

27. A method of manufacturing a flexible tubular body for a catheter or sheath, the method comprising:
    forming a flexible tubular body having an inner layer and an outer layer, said flexible tubular body comprising a polymer;
    forming a wire lumen extending along at least a portion of the flexible tubular body in at least one of the inner layer and the outer layer adjacent an interface between the inner layer and the outer layer;
    placing a deflection wire in the wire lumen; and
    injecting a fluid into the wire lumen with the deflection wire in the wire lumen.

28. The method according to claim 27, further comprising sealing one end of the wire lumen such that the fluid does not flow therethrough.

29. The method according to claim 27, further comprising melt-processing the flexible tubular body with the fluid in the wire lumen, wherein the fluid is injected at a pressure sufficient to resist collapse of the wire lumen during the step of melt-processing the flexible tubular body.

30. The method according to claim 29, wherein the fluid is injected at a pressure between about 50 psig and about 110 psig.

31. A method of manufacturing a catheter having flexible tubular body, the method comprising:
    forming a lumen having an inner diameter large enough to accept a deflection wire therethrough;
    inserting a deflection wire into the lumen;

pressurizing the lumen to a pressure sufficient to resist collapse of the wire lumen during lamination of the flexible tubular body via heating;

applying a layer of shrink-wrap about the flexible tubular body to exert pressure on and prevent expansion of the flexible tubular body during heating thereof; and heating the flexible tubular body while the lumen is pressurized and contains the deflection wire.

32. A method of manufacturing a flexible tubular body for a catheter or sheath, the flexible tubular body comprising a melt-processable polymer, the method comprising:

providing an inner layer;

applying an outer layer about the inner layer;

forming a wire lumen in at least one of the inner layer and the outer layer adjacent an interface between the inner layer and the outer layer;

injecting a fluid into the wire lumen; and melt-processing the flexible tubular body to bond the inner layer and the outer layer together while the fluid is in the wire lumen.

* * * * *